US010133092B2

United States Patent
Tsubota et al.

(10) Patent No.: US 10,133,092 B2
(45) Date of Patent: Nov. 20, 2018

(54) MYOPIA PREVENTION DEVICE

(71) Applicant: TSUBOTA LABORATORY, INC., Tokyo (JP)

(72) Inventors: Kazuo Tsubota, Funabashi (JP); Kazuno Negishi, Tokyo (JP); Hidemasa Torii, Yokohama (JP); Toshihide Kurihara, Tokyo (JP)

(73) Assignee: TSUBOTA LABORATORY, INC., Tokyo (JP)

( * ) Notice: Subject to any disclaimer, the term of this patent is extended or adjusted under 35 U.S.C. 154(b) by 0 days.

(21) Appl. No.: 15/366,558

(22) Filed: Dec. 1, 2016

(65) Prior Publication Data
US 2017/0168320 A1 Jun. 15, 2017

Related U.S. Application Data

(63) Continuation-in-part of application No. PCT/JP2015/065997, filed on Jun. 3, 2015.

(30) Foreign Application Priority Data

Jun. 3, 2014 (JP) .................................. 2014-115286

(51) Int. Cl.
*G02C 7/14* (2006.01)
*G02C 3/00* (2006.01)
(Continued)

(52) U.S. Cl.
CPC ................ *G02C 7/104* (2013.01); *F21V 9/00* (2013.01); *G02C 11/04* (2013.01); *G02C 2202/24* (2013.01)

(58) Field of Classification Search
CPC .... G02C 7/104; G02C 11/04; G02C 2202/24; F21V 9/00
(Continued)

(56) References Cited

U.S. PATENT DOCUMENTS

| 5,284,843 A | 2/1994 | Stone et al. |
| 5,571,823 A | 11/1996 | Stone et al. |

(Continued)

FOREIGN PATENT DOCUMENTS

| JP | H01-299560 A | 12/1989 |
| JP | H06-502839 A | 3/1994 |

(Continued)

OTHER PUBLICATIONS

Lougheed, T., The Evidence for Environmental Factors, Jan. 1, 2014, vol. 122(1), A12-A19, Environmental Health Perspectives.

(Continued)

*Primary Examiner* — Tuyen Tra
(74) *Attorney, Agent, or Firm* — Oblon, McClelland, Maier & Neustadt, L.L.P.

(57) ABSTRACT

The purpose of the present invention is to provide a myopia prevention device. A myopia prevention device of the present invention comprises a light transmission part selected from a group consisting of an eyesight correcting tool, an eye protection tool, a face protection tool, a sunshade, a display device, a window, a wall, a light source covering, and a coating material. The light transmission part of the device transmits light having a wavelength within a range of 350 nm to 400 nm inclusive and thus suppresses the occurrence and progression of myopia. Further, a myopia prevention device comprises a light emission part selected from a group consisting of lighting equipment, a display device, and a light irradiation device. The light emission part of the device emits light having a wavelength within a range of 350 nm to 400 nm inclusive and thus suppresses the occurrence and progression of myopia.

10 Claims, 19 Drawing Sheets

(51) Int. Cl.
  *G02C 7/02* (2006.01)
  *G02C 7/10* (2006.01)
  *F21V 9/00* (2018.01)
  *G02C 11/04* (2006.01)

(58) Field of Classification Search
  USPC ............ 351/159.65, 159.6, 159.01, 41
  See application file for complete search history.

(56) References Cited

U.S. PATENT DOCUMENTS

| | | |
|---|---|---|
| 2003/0162929 A1 | 8/2003 | Verbruggen et al. |
| 2007/0203317 A1 | 8/2007 | Verbruggen et al. |
| 2008/0015660 A1 | 1/2008 | Herekar |
| 2009/0146569 A1 | 6/2009 | Krijnen et al. |
| 2014/0081357 A1 | 3/2014 | Legerton et al. |
| 2015/0142086 A1 | 5/2015 | Narita |

FOREIGN PATENT DOCUMENTS

| | | |
|---|---|---|
| JP | 7-24052 A | 1/1995 |
| JP | H09-292848 A | 11/1997 |
| JP | 2001-133625 A | 5/2001 |
| JP | 2005-516702 A | 6/2005 |
| JP | 2010-506601 A | 3/2010 |
| JP | 2015-096155 A | 5/2015 |
| WO | 1989/011854 A1 | 12/1989 |
| WO | 1997/18270 A1 | 5/1997 |
| WO | 2003/066707 A1 | 8/2003 |
| WO | WO 2006/056934 A2 | 6/2006 |
| WO | 2008/008914 A2 | 1/2008 |
| WO | WO 2013/188825 A1 | 12/2013 |
| WO | 2014/036133 A1 | 3/2014 |
| WO | 2015/010920 A1 | 1/2015 |

OTHER PUBLICATIONS

Stephen B. Prepas, Light, literacy and the absence of ultraviolet radiation in the development of myopia, Medical Hypotheses (2008), Sep. 4, 2007, vol. 70, No. 3, p. 635-637, Elsevier.
Regan S. Asbby, Frank Schaeffel, The Effect of Bright Light on Lens Compensation in Chicks, IOVS, Oct. 2010, vol. 51, No. 10, p. 5247-5253, Investigative Ophthalmology & Visual Science.
Saito et al., Protective Effects of Metallothionein I and II Against Metal- and Ultraviolet Radiation-Induced Damage in Cultured Lens Epithelial Cells, Japanese Journal of Ophthalmology, Sep. 2010, vol. 54, p. 486-493, Japanese Ophthalmological Society.
Per G. Soderberg, Optical radiation and the eyes with special emphasis on children, Progress in Biophysics and Molecular Biology, Sep. 2011, 107, p. 389-392, Elsevier.
Ian G Morgan et al., Myopia, Ophthalmology 2, May 5, 2012, vol. 379, p. 1739-1748, The Lancet.
Iwase, A. et al., Prevalence and Causes of Low Vision and Blindness in a Japanese Adult Population, the Tajimi Study, Ophthalmology, Apr. 2006, p. 1354-1362, Elsevier.
Written Opinion of the International Search Authority for PCT/JP2015/065997 dated Aug. 25, 2015.
Extended European Search Report dated Dec. 15, 2017 in European Patent Application No. 15803562.6, citing documents AO, AP, and AQ, 9 pages.
H. Burkhard Dick, et al., "Foldable Artiflex Phakic Intraocular Lens for the Correction of Myopia", Ophthalmology, vol. 116 No. 4, XP026080521, Apr. 1, 2009, pp. 671-677.
Stephen B. Prepas, "Light, Literacy and the Absence of Ultraviolet Radiation in the Development of Myopia", Medical Hypotheses, vol. 70 No. 3, XP022449003, Jan. 1, 2008, pp. 635-637.

Fig. 5

| Irradiation distance h | Irradiation strength at point P mW/cm2 |
|---|---|
| 100 | 2.5 |
| 90 | 2.7 |
| 80 | 3.1 |
| 70 | 3.5 |
| 60 | 4.1 |
| 50 | 5.0 |

MYOPIA PREVENTION DEVICE

CROSS REFERENCE TO RELATED APPLICATIONS

This application is a Continuation-in-Part Application of International Application No. PCT/JP2015/065997 filed Jun. 3, 2015, claiming priority based on Japanese Patent Application No. 2014-115286, filed Jun. 3, 2014, the contents of all of which are incorporated herein by reference in their entirety.

FIELD OF THE INVENTION

The present invention relates to a myopia prevention device that suppresses the occurrence and progression of myopia.

BACKGROUND ART

The eye reportedly incurs various damage when exposed to ultraviolet light (Saito et al., Jpn Opthalmol 2010; 54: 486-493, Per G. Soderberg, Progress in Biophysics and Molecular Biology 107 (2011) 389-392). As a result, many products, such as eyeglasses and contact lenses, that minimize the transmission of ultraviolet light to the extent possible to prevent excessive eye exposure to ultraviolet light are now commercially available.

Meanwhile, the number of persons with myopia is reportedly still increasing worldwide. Myopia includes refractive myopia and axial myopia, many cases being axial myopia. With axial myopia, myopia progresses in association with elongation of an axial length of the eye, and the elongation is irreversible (Morgan I G et al., Lancet, 2012). When myopia progresses, high myopia occurs, and high myopia is known as the leading cause of blindness (Iwase A. et al., Ophthalmology, 2006). For this reason, there has been strong demand for means for preventing the occurrence of myopia and means for suppressing the progression of myopia.

SUMMARY OF THE INVENTION

Problems to be Solved by the Invention

It is therefore an object of the present invention to provide a myopia prevention device that suppresses the occurrence and progression of myopia.

Means for Solving the Problems

The present inventors were the first to discover that a degree of elongation of the axial length of an eye exposed to light having a wavelength within a range of 350 nm to 400 nm inclusive is significantly small compared to the degree of elongation of the axial length of an eye not exposed to light having a wavelength of 400 nm or less, and the degree of myopia related to the refractive value of the eye decreases. That is, the present inventors were the first to discover that it is possible to suppress the occurrence and progression of myopia by exposing the eye to light having a wavelength within that specified range. The present invention addresses the problem of providing a myopia prevention device that ensures eye exposure to light having a wavelength within the range of 350 nm to 400 nm inclusive.

Examples of a myopia prevention device according to the present invention include a device comprising a light transmission part that transmits light (light having a wavelength within the range of 350 nm to 400 nm inclusive), and a device comprising a light emission part which emits light (light having a wavelength within the range of 350 nm to 400 nm inclusive). An example of the device comprising the light transmission part is as follows: a device selected from a group consisting of an eyesight correcting tool, an eye protection tool, a face protection tool, a sunshade, a display device, a window, a wall, a light source covering, and a coating material. On the other hand, an example of the device comprising the light emission part is as follows: a device selected from a group consisting of light equipment, a display device, and a light irradiation device. The myopia prevention device may be any one of the devices that transmit or emit the specified light, or may be a combination of these devices used as a set.

A first embodiment of the present invention is a myopia prevention device comprising a light transmission part selected from a group consisting of an eyesight correcting tool, an eye protection tool, a face protection tool, a sunshade, a display device, a window, a wall, a light source covering, and a coating material. The light transmission part of the device transmits light having a wavelength within a range of 350 nm to 400 nm inclusive, and thus suppresses the occurrence and progression of myopia.

A second embodiment of the present invention is a myopia prevention device comprising a light emission part selected from a group consisting of lighting equipment, a display device, and a light irradiation device. The light emission part of the device emits light having a wavelength within a range of 350 nm to 400 nm inclusive, and thus suppresses the occurrence and progression of myopia.

A third embodiment of the present invention is a method for investigating if light having a predetermined wavelength within a range of 350 nm to 400 nm inclusive can prevent myopia (including methods in which an animal serves as the subject).

A fourth embodiment of the present invention is a myopia prevention method for irradiating light having a wavelength within a range of 350 nm to 400 nm inclusive (including methods in which an animal serves as the subject).

A fifth embodiment of the present invention is a set of a myopia prevention device comprising a light transmission part that transmits light having a wavelength within a range of 350 nm to 400 nm inclusive, and a myopia prevention device comprising a light emission part that emits light having a wavelength within a range of 350 nm to 400 nm inclusive. An example of such a set is as follows: a set of a myopia prevention device comprising a light transmission part selected from a group consisting of an eyesight correcting tool, an eye protection tool, a face protection tool, a sunshade, a display device, a window, a wall, a light source covering, and a coating material, and a myopia prevention device comprising a light emission part selected from a group consisting of lighting equipment, a display device, and a light irradiation device.

BRIEF DESCRIPTION OF THE DRAWINGS

FIG. 5 is a table showing the relationship between the intensity of light emitted by the irradiation device used in Example 2, and a distance from the irradiation device.

EMBODIMENTS OF THE INVENTION

Figure 1:
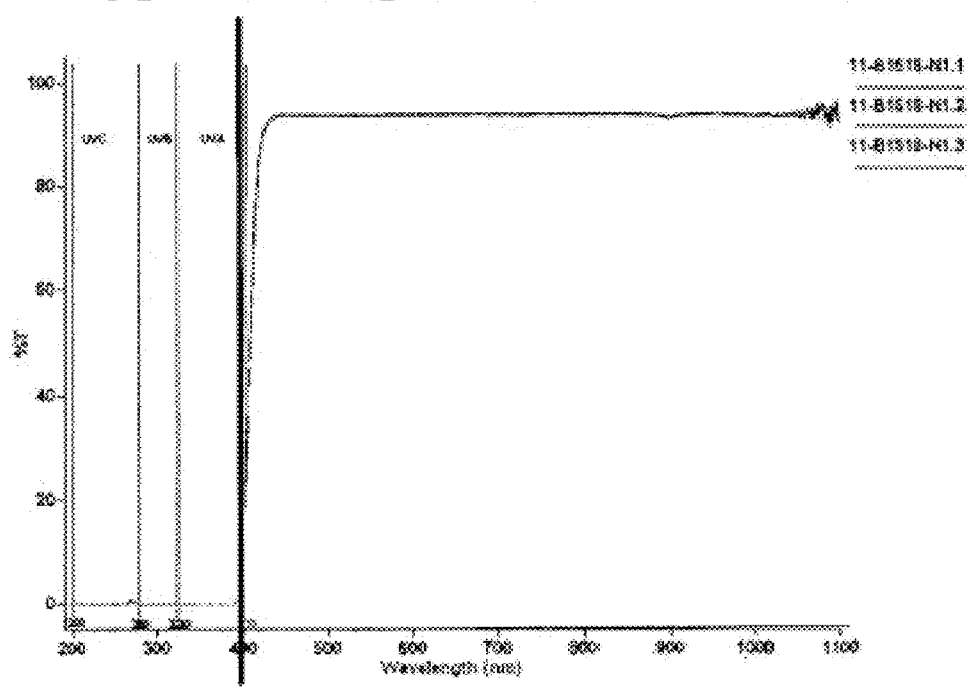
FIG. 1 is a graph showing a spectral transmission curve of an intraocular lens (brand name: Artisan) used in Example 1.

The following describes in detail embodiments of the present invention that were completed on the basis of the discovery described above while providing examples. Note that the object, features, advantages, and ideas of the present invention are apparent to those skilled in the art from the descriptions herein. Furthermore, those skilled in the art can easily reproduce the present invention from these descriptions. The embodiments and the specific examples described below represent preferable modes of the present invention, which are given for the purpose of illustration or description. The present invention is not limited thereto. It is obvious to those skilled in the art that various changes and modifications may be made according to the descriptions of the present specification without departing from the spirit and scope of the present invention disclosed herein.

In the present specification, "to prevent myopia" means to prevent the occurrence of myopia and to suppress the progression of myopia. Thus, a "myopia prevention device" means a device for preventing the occurrence of myopia, and a device for suppressing the progression of myopia.

The present invention prevents myopia by ensuring that the eye is exposed to light having a wavelength within a range of 350 nm to 400 nm inclusive.

In the present invention, "350 nm to 400 nm inclusive" may be light across all wavelengths within that range (350 to 400 nm), or light across a portion of wavelengths within the range. An example of a portion of wavelengths within the range is 360 nm to 400 nm inclusive (shown in FIG. 11), and the device may be a device that transmits or emits light of this range.

(1) Myopia Prevention Device Comprising Light Transmission Part

The myopia prevention device according to the present invention comprises a light transmission part that transmits light having a wavelength within a range of 350 nm to 400 nm inclusive among the wavelengths of light such as natural light and artificial light. The light transmission part transmits light having a wavelength within a range of 350 nm to 400 nm inclusive and acts so as to suppress the occurrence and progression of myopia.

The light transmission part is preferably made of a material that does not transmit light having a wavelength of 315 nm or less, a value that may be harmful to the eye, and is more preferably made of a material that transmits only light having a wavelength (within the range of 350 nm to 400 nm inclusive) effective in preventing myopia and not light having a wavelength less than 350 nm. Note that, weak light that will not affect the eye (light at the edge of the spectrum and noise-like light), even light having a wavelength less than 350 nm, may be included, but even in such a case light of 315 nm or less is preferably not included. This light transmission part may be one part that transmits light having a wavelength within the range of 350 nm to 400 nm inclusive and not light having a wavelength of 315 nm or less (preferably less than 350 nm), or may be a combination of a part that transmits light having a wavelength within the range of 350 nm to 400 nm inclusive, and a part that does not transmit light having a wavelength of 315 nm or less (preferably less than 350 nm).

Specific examples include the following, but the present invention is not limited thereto: eyesight correcting tools (eyeglass lenses, contact lenses, intraocular lenses, and the like), eye protection tools (sunglasses, protective glasses, goggles, and the like), face protection tools (helmet shields and the like), sunshades (umbrellas, sunvisors, and the like), display screens of display devices (televisions, PC monitors, gaming devices, portable media players, cell phones, tablet terminals, wearable devices, 3D glasses, virtual glasses, mobile book readers, car navigation systems, imaging devices such as digital cameras, monitors inside vehicles, monitors inside airplanes, and the like), curtains (cloth curtains, vinyl curtains, and the like), windows (windows of a building or airplane; front, rear, or side windows of a vehicle; and the like), walls (glass curtain walls and the like), light source coverings (light covers and the like), and coating materials (seals, coating liquids, and the like).

Here, the intraocular lens refers to an artificial crystalline lens inserted when a crystalline lens is removed, or a phakic intraocular lens inserted for the purpose of myopia correction.

The material of the light transmission part is not particularly limited as long as the material is capable of performing processing so that light having a wavelength within the range of 350 nm to 400 nm inclusive is transmitted, and light having a wavelength of 315 nm or less (preferably light having a wavelength less than 350 nm) is not transmitted, Examples include glass and plastic. Further, a light absorber that substantially absorbs light having a wavelength of 315 nm or less (preferably light having a wavelength less than 350 nm), a light scattering agent, or the like may be used.

In the case of "light is not transmitted" described above, the light transmission rate is preferably 1% or less, and more preferably 0.1% or less. Methods for measuring the light transmission rate are well known to those skilled in the art, and measurement can be performed using any known measuring device and method.

The transmission rate of light having a wavelength within the range of 350 nm to 400 nm inclusive may be selected as appropriate according to the amount of surrounding light, but is preferably 21% or greater, and more preferably 30% or greater.

An irradiance at which the transmitted light having a wavelength within the range of 350 nm to 400 nm inclusive reaches the eye may be 5.0 mW/cm$^2$ or less. Preferred irradiances are 3.0 mW/cm$^2$ or less, 1.0 mW/cm$^2$ or less, 0.5 mW/cm$^2$ or less, and 0.25 mW/cm$^2$ or less, in that order. On the other hand, the irradiance is preferably set taking into consideration the effect on the human eye and skin. When a person is exposed to light for a long period of time for the purpose of myopia prevention, the irradiance relates to exposure time as well, and may be increased if the time is short, but is preferably decreased if the time is long. The irradiance is preferably 1.0 mW/cm$^2$ or less, and is preferably decreased to 0.5 mW/cm$^2$ or less, 0.1 mW/cm$^2$ or less, and 0.05 mW/cm$^2$ or less as the time increases. The irradiance can be measured using a known method.

The myopia prevention device that comprises the light transmission part according to the present invention may transmit light having a wavelength greater than 400 nm. The transmission rate thereof is not particularly limited.

(2) Myopia Prevention Device Comprising Light Emission Part

The myopia prevention device according to the present invention comprises the light emission part that emits light having a wavelength within the range of 350 nm to 400 nm inclusive. The light emission part emits light having a wavelength within the range of 350 nm to 400 nm inclusive and acts so as to suppress the occurrence and progression of myopia. Specific examples of the myopia prevention device that comprises the light emission part are as follows, but the present invention is not limited thereto: lighting equipment (room lights, lights inside vehicles, lights inside airplanes, street lights, floor lamps, spotlights, and the like), display screens provided to various display devices (for example, televisions, PC monitors, gaming devices, portable media players, cell phones, tablet terminals, wearable devices, 3D glasses, virtual glasses, mobile book readers, car navigation systems, digital cameras, monitors inside vehicles, monitors inside airplanes, and the like), and light irradiation devices used for myopia prevention.

Figure 11:
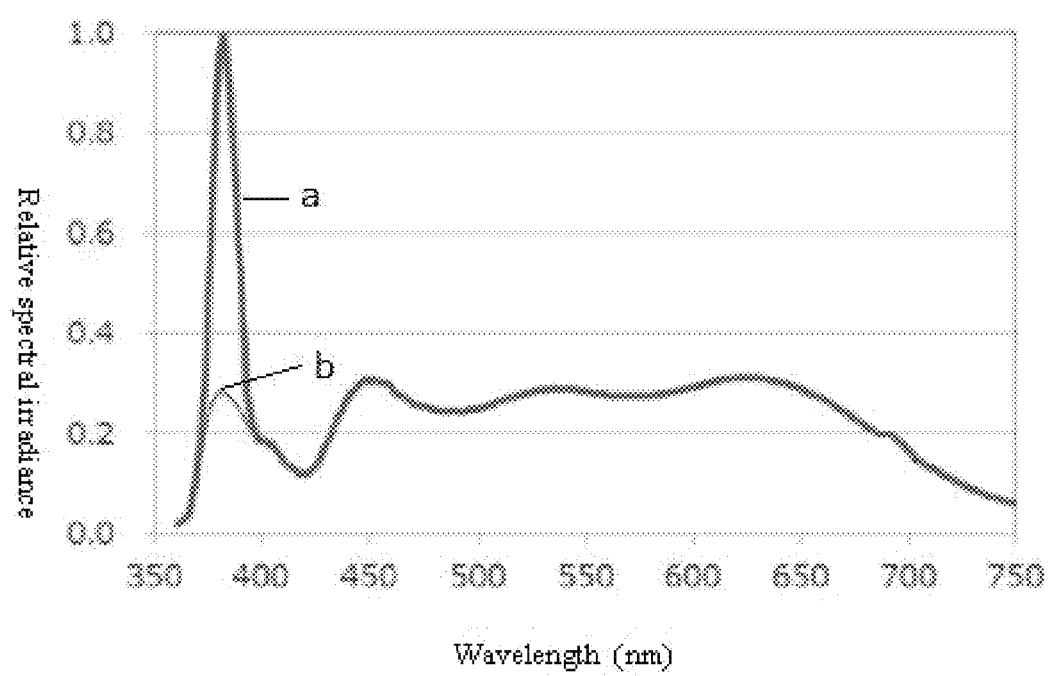
FIG. 11 is an optical spectrum of a lamp that emits light having a wavelength within a range of 350 nm to 400 nm inclusive in Example 4.

The light emission part may further produce light having a wavelength greater than 400 nm. For example, as illustrated in FIG. 11, the light emission part may emit light having a wavelength within the range of 350 nm to 400 nm inclusive in combination with light having a wavelength greater than 400 nm. Light having a wavelength greater than 400 nm may be emitted from a light emission part other than the light emission part that emits light having a wavelength of 350 nm to 400 nm inclusive, or may be emitted along with the light having a wavelength of 350 nm to 400 nm inclusive from the same light emission part. With light having a wavelength greater than 400 nm, the hue of the overall light emitted from one or two or more light emission parts can be adjusted depending on the wavelength range of the light, and thus preferably light of the specified wavelength range corresponding to the desired hue is emitted.

Figure 18:
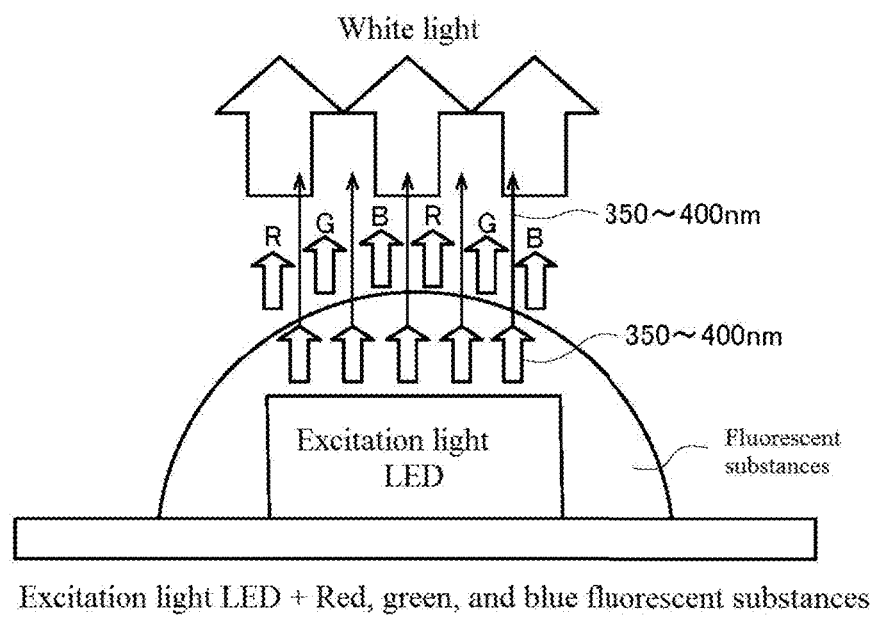
FIG. 18 is a schematic view illustrating an example of a light-emitting device comprising a light emission part (LED) that emits excitation light having a wavelength within a range of 350 nm to 400 nm inclusive.

Examples of such a light emission part include the light-emitting device illustrated in FIG. 18. The light-emitting device illustrated in FIG. 18 comprises a light emission part (LED) that emits excitation light having a wavelength within the range of 350 nm to 400 nm inclusive. This light-emitting device is a configuration example with an excitation light emission part (LED) that emits excitation light having a wavelength within the range of 350 nm to 400 nm inclusive, and fluorescent substances of red, green, and blue provided so as to cover the excitation light emission part. With such a configuration, the fluorescent substances emit white light when the excitation light having a wavelength within the range of 350 nm to 400 nm inclusive is irradiated on the fluorescent substances. Further, a portion of the light (excitation light) having a wavelength within the range of 350 nm to 400 nm inclusive transmits the fluorescent substances as illustrated. Such a light-emitting device can be used as a white light source and as an application for producing the myopia prevention effect.

Figure 19:
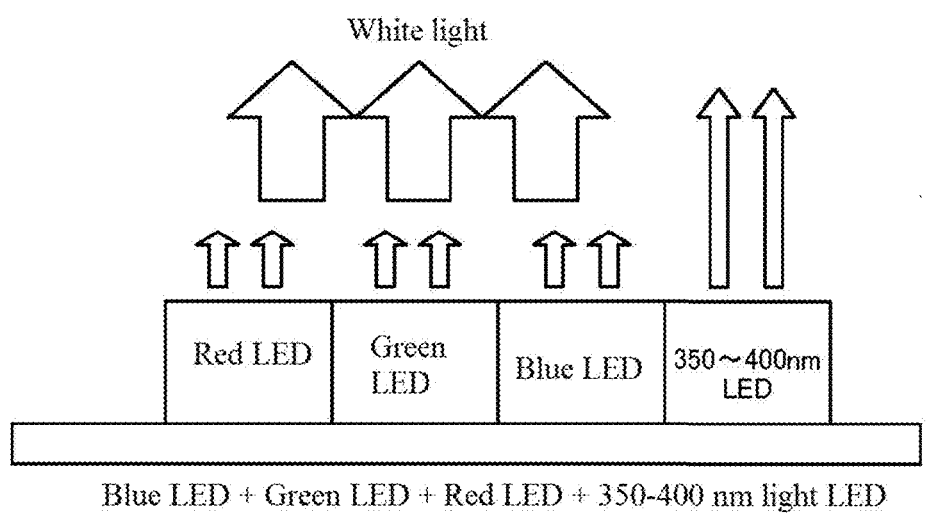
FIG. 19 is a schematic view illustrating an example of an RGB light-emitting device comprising the light emission part (LED) that emits light having a wavelength within a range of 350 nm to 400 nm inclusive.

Further, examples of such a light emission part also include the light-emitting device illustrated in FIG. 19. The light-emitting device illustrated in FIG. 19 is an RGB light-emitting device comprising a light emission part (LED) that emits light having a wavelength within the range of 350 nm to 400 nm inclusive. This light-emitting device is a configuration example with the light emission part that emits light having a wavelength within the range of 350 nm to 400 nm inclusive, and light emission parts (LED) of red (R), green (G), and blue (B). Such a configuration results in the advantages of emitting light having a wavelength within the range of 350 nm to 400 nm inclusive and thus producing the myopia prevention effect, and emitting white light from the RGB light-emitting device and thus being able to utilize the device as a white light source indoors or the like. It should be noted that light having a wavelength within the range of 350 nm to 400 nm inclusive can be turned ON and OFF as necessary, and can be emitted for a required time to produce the myopia prevention effect when necessary.

General RGB light-emitting devices can create pseudo white light close to sunlight, but such white light does not substantially include light within the range of 350 nm to 400 nm inclusive. Nevertheless, the light-emitting devices illustrated in FIG. 18 and FIG. 19 are capable of emitting light within the range of 350 nm to 400 nm inclusive and constitute non-pseudo white light (natural light) close to sunlight having a broad spectral width, and produce the exceptional effect of selectively emitting light within the range of 350 nm to 400 nm inclusive, which particularly has the myopia prevention effect. It should be noted that white light may be emitted using the means illustrated in FIG. 18 and FIG. 19, or may be emitted using other means. Examples of other means include a light-emitting device (B not included) made of R (red) and G (green) for which light emission wavelengths are controlled.

Figure 4:
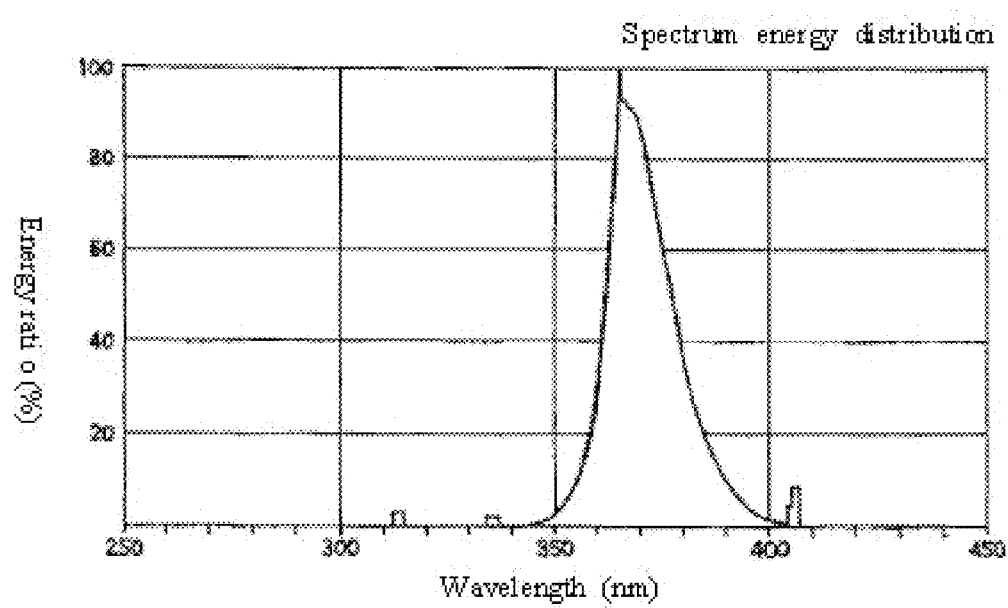
FIG. 4 is a graph showing the relationship between an intensity and a wavelength of light emitted by an irradiation device used in Example 2.

Further, when the myopia prevention device comprises the light emission part that emits light having a wavelength of 350 nm to 400 nm inclusive, preferably light having a wavelength less than 350 nm is not produced (refer to FIG. 4 and FIG. 11). It should be noted that, more preferably, even if light less than 350 nm is slightly emitted in a noise-like manner, light having a wavelength of 315 nm or less that may be harmful to the eye is not emitted.

The irradiance at which the light having a wavelength within the range of 350 nm to 400 nm inclusive and emitted from the light emission part reaches the eye is not particularly limited, but may be 5.0 mW/cm$^2$ or less. The preferred irradiance is 3.0 mW/cm$^2$ or less. On the other hand, the irradiance is preferably set taking into consideration the effect on the human eye and skin. When light is emitted toward a person for a long period of time for the purpose of myopia prevention, the irradiance relates to the light emission time as well, and may be increased if the time is short, but is preferably decreased if the time is long. The irradiance is preferably 1.0 mW/cm$^2$ or less, and is preferably decreased to 0.5 mW/cm$^2$ or less, 0.1 mW/cm$^2$ or less, and 0.05 mW/cm$^2$ or less as the time increases. The irradiance can be measured using a known method. It should be noted that "irradiance" means the intensity of the light that enters or reaches the eye.

It should be noted that the myopia prevention device comprising the light emission part according to the present invention may be a myopia prevention set combined with the myopia prevention device comprising the light transmission part described above. Accordingly, a more superior myopia prevention effect is exhibited more safely. When the devices are combined, the irradiance of the light emitted from the light emission part may be adjusted in accordance with the light transmission characteristics of the myopia prevention device comprising the light transmission part. For example, when the light transmission part controls the permeability of light having a wavelength within the range of 350 nm to 400 nm inclusive, the irradiance emitted from the light emission part may be set higher than the irradiance values described above. On the other hand, when the light transmission part does not control the permeability of light having a wavelength within the range of 350 nm to 400 nm inclusive, the irradiance emitted from the light emission part may be adjusted within the range of the irradiance values described above.

(3) Myopia Prevention Method

A first myopia prevention method of the present invention is mounting the myopia prevention device that comprises the light transmission part described above. The mounting method is not particularly limited, and thus the myopia prevention device may be mounted as appropriate in accordance with the type of myopia prevention device.

A second myopia prevention method of the present invention is using the myopia prevention device that comprises the light emission part described above. The method of use is not particularly limited, and thus the myopia prevention device may be used as appropriate in accordance with the type of myopia prevention device. If the myopia prevention device is a daily necessity such as a room light, the room light may be simply used in daily life without a special method of use. Further, if the device is a light irradiation device used for myopia prevention, the device may be used so that the light irradiated from the irradiation device enters the eye for a certain period of the day.

A third myopia prevention method of the present invention is mounting the myopia prevention device that comprises the light transmission part described above while using the myopia prevention device that comprises the light emission part described above. According to this method, a more superior myopia prevention effect is exhibited more safely.

It should be noted that these methods can be applied to a human as well as a vertebrate other than a human.

(4) Method for Investigating Light Suitable for Myopia Prevention

The method for identifying light suitable for myopia prevention is a method for investigating if light having a predetermined wavelength within the range of 350 nm to 400 nm inclusive can prevent myopia, and includes the step of irradiating light having that wavelength on a human or a vertebrate other than a human, and further includes the step of irradiating such light on a cell or gene extracted from the human or the vertebrate other than the human. Then, whether or not such a wavelength can actually prevent myopia is investigated using the method set forth in Example 2, for example. This makes it possible to identify which wavelength or wavelength range within the range of 350 to 400 nm inclusive has a particularly high effect. Further, examples of cases when such light is irradiated on a cell or a gene extracted from a human or a vertebrate other than a human include verification of increased manifestation of myopia suppressor gene EGR1 using retinal visual cell line 661W derived from a human.

EXAMPLES

Example 1

Using a phakic intraocular lens as an example of the myopia prevention device that comprises the light transmission part that transmits or substantially transmits light having a wavelength within the range of 350 nm to 400 nm inclusive, and does not or substantially does not transmit light having a wavelength less than 350 nm, the myopia prevention effect was verified by the test described below.

First, the axial length of the eye was measured, and then the phakic intraocular lens Artisan (brand name) Model 204 (Ophtec BV) that substantially does not transmit light across the full spectrum of wavelengths of approximately 400 nm or less, or the phakic intraocular lens Artiflex (brand name) Model 401 (Ophtec BV) that transmits light having a wavelength within the range of 350 to 400 nm inclusive was surgically inserted into the measured eye. Subsequently, the elongation of the axial length of the eye was measured five years after the insertion procedure. The axial length of the eye was measured using IOL Master (Carl Zeiss Meditec) by a standard method.

Figure 2:
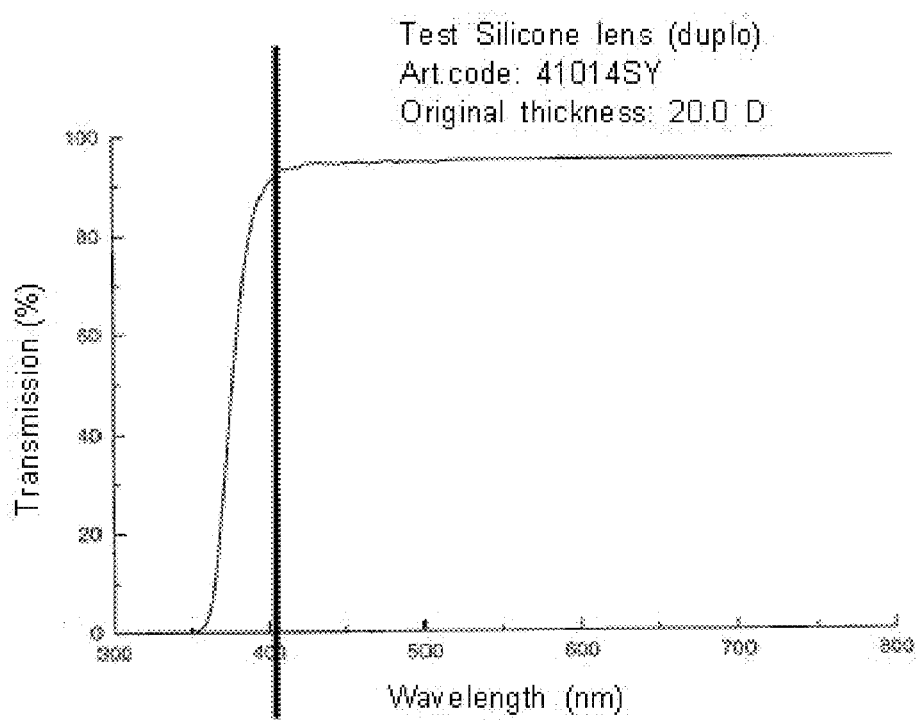
FIG. 2 is a graph showing a spectral transmission curve of an intraocular lens (brand name: Artiflex) used in Example 1.

FIG. 1 shows the Artisan (brand name) spectral transmission curve, and FIG. 2 shows the Artiflex (brand name) spectral transmission curve.

Meanwhile, as control eyes, the degrees of elongation over a two-year period of the axial lengths of 185 eyes with high myopia that have not undergone refractive surgery were measured, and the average value was found. The elongation of the axial lengths of the control eyes was 0.065 mm/year on average (for details, refer to Saka N, et al., Graefes Arch Clin Exp Ophthalmol., Vol. 251, pp. 495-499, 2013). The axial length of the eye was measured using the same IOL Master as described above.

Figure 3:
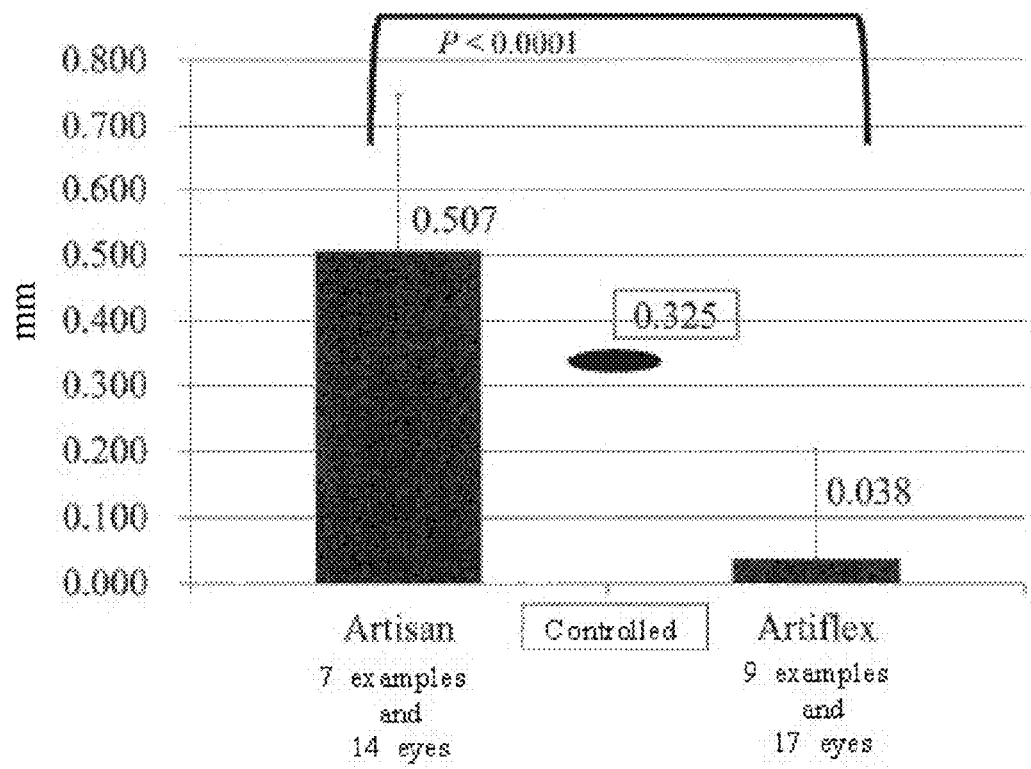
FIG. 3 is a graph showing degrees of elongation of an axial length of control eyes and eyes into which one of two types of intraocular lenses was inserted in Example 1.

FIG. 3 shows the degrees of elongation over a five-year period of the axial lengths of 7 examples and 14 eyes (average age: 35.7 years) that used Artisan (brand name), 9 examples and 17 eyes (average age: 36.1 years) that used Artiflex (brand name), and the control eyes (185 eyes; average age: 48.4 years). For the eyes that used Artisan (brand name) and the eyes that used Artiflex (brand name), the difference in the axial length of the eye before and after the insertion procedure was set as the degree of elongation of the axial length over the five-year period. For the control eyes, the value obtained by multiplying the average elongation of the axial length over one year found by the above by 5 was set as the degree of elongation of the axial length over the five-year period.

As shown in FIG. 3, the degree of elongation of the axial length of the eye exposed to light having a wavelength within the range of 350 to 400 nm inclusive was significantly smaller than that of the eye that was essentially not exposed to light across the full spectrum of wavelengths of approximately 400 nm or less.

Example 2

Using an irradiation device that irradiates light having a wavelength within a range of 350 nm to 400 nm inclusive as an example of the myopia progression prevention device that comprises the light emission part that emits light having a wavelength within the range of 350 nm to 400 nm inclusive, the myopia prevention effect was verified by the test described below.

A chick is known to develop myopia in an eye (shielded eye) that is covered with a transparent hemisphere (refer to Seko, et al., Invest. Ophthalmol. Vis. Sci., May 1995, Vol. 36, No. 6, 1183-1187, for example). Hence, one eye of each of 30 White Leghorn chicks was covered with a transparent hemisphere six days after birth. The chicks were divided into a non-irradiation group of 15 that were not irradiated with light having a wavelength within the range of 350 nm to 400 nm inclusive, and an irradiation group of 15 that were irradiated with light having a wavelength within the range of 350 nm to 400 nm inclusive. The chicks were then each inserted into a cage having the dimensions of a 450-mm length, an 800-mm width, and a 250-mm height, and raised for one week spending 12 hours in the light and 12 hours in the dark each day. The degree of myopia development of the shielded eye was then examined.

The irradiation of light having a wavelength within the range of 350 nm to 400 nm inclusive (peak wavelength: 365 nm) was performed using the UV lamp PL-S TL/08 (Phillips) at an output of 1.7 W. It should be noted that this lamp is used in applications such as non-destructive testing, insect capturing, banknote discrimination, medicine, and displays.

FIG. 4 shows the spectrum energy distribution of the irradiation device, and FIG. 5 shows the relationship between the irradiance (mW/cm$^2$) of the irradiated light and the distance h (mm) from the lamp. It should be noted that the light source was installed at a distance of approximately 80 mm from the chicks. The chicks hopped up and down, and thus the distance from the light source to the chicks was about 50 mm when closest.

The refractive value, vitreous cavity length, and the axial length of the shielded eye of each of 14 chicks in the non-irradiation group and 13 chicks in the irradiation group were measured 13 days after birth (one week after shielding was started). The refractive value was measured using an autorefractometer by a standard method. The vitreous cavity length and the axial length of the eye were measured using US-4000 (Nidek) in mode B.

Figure 6:
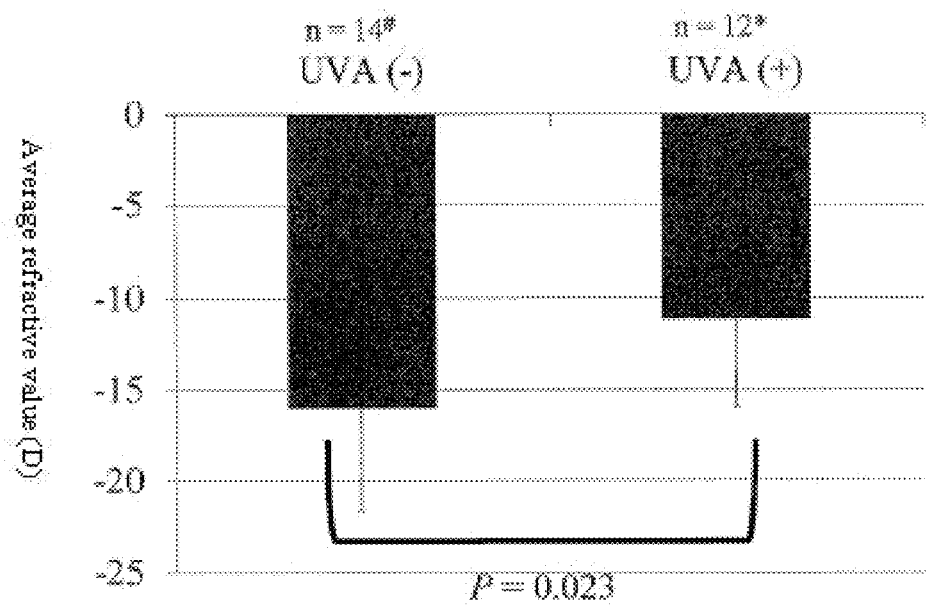
FIG. 6 is a graph showing refractive values of eyes of chicks irradiated with light and eyes of chicks not irradiated with light in Example 2.
Figure 7:
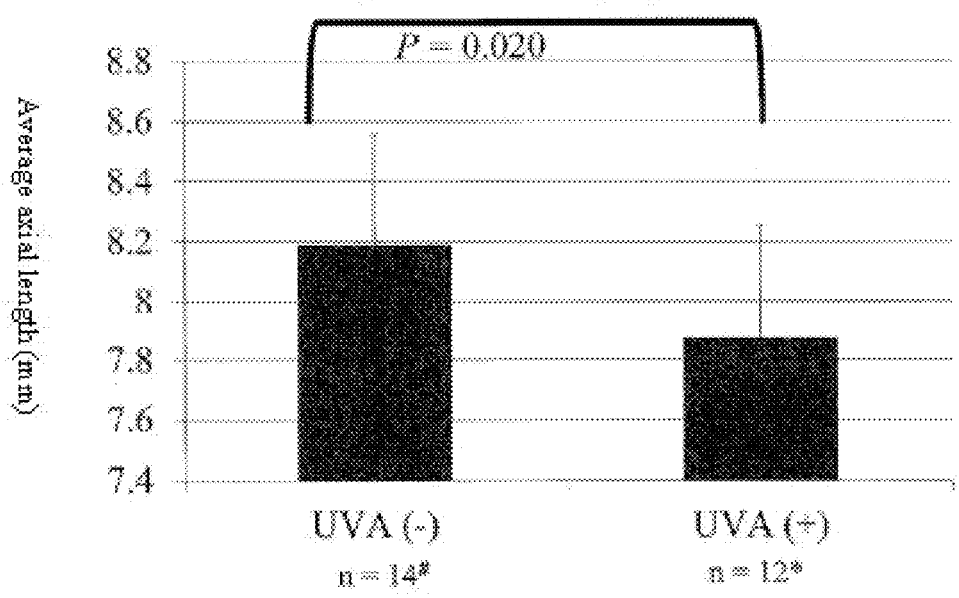
FIG. 7 is a graph showing the axial lengths of eyes of chicks irradiated with light and eyes of chicks not irradiated with light in Example 2.

FIG. 6 shows the results of refractive value measurements, and FIG. 7 shows the results of axial length measurement. A Mann-Whitney U test was used for the significance test. In the figures, the expression "UVA (−)" indicates non-irradiation, and the expression "UVA (+)" indicates irradiation.

As shown in FIG. 6, the average refractive value of the shielded eyes of the irradiation group was significantly large compared to the average refractive value of the shielded eyes of the non-irradiation group (there was a myopia prevention effect from irradiation of light having a wavelength within the range of 350 nm to 400 nm inclusive). Further, as shown in FIG. 7, the average axial length of the shielded eyes of the irradiation group was significantly small compared to the average axial length of the shielded eyes of the non-irradiation group. Thus, it was clear that the degree of myopia of the irradiation group was significantly small compared to that of the non-irradiation group. Further, based on the values of intensity shown in FIGS. 4 and 5, the myopia prevention effect was achieved at a relatively low intensity.

Example 3

Figure 8:
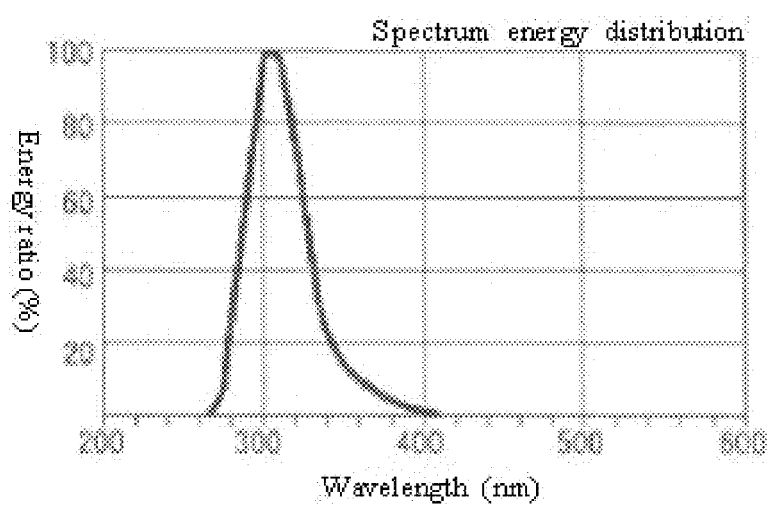
FIG. 8 is a graph showing the relationship between an intensity and a wavelength of light having a peak at 305 nm and emitted by an irradiation device used in Example 3.

When light having a peak at 305 nm (FIG. 8) was irradiated for two days on chicks five days after birth, epithelium inflammation was formed on the corneas of the chicks. Thus, light having a wavelength of 315 nm or less has potent tissue damage properties, and thus the light irradiated for myopia prevention preferably does not include light having a wavelength of 315 nm or less, is preferably light having a wavelength of 340 nm or greater, and more preferably light having a wavelength of 350 nm or greater.

Example 4

To achieve a myopia suppression effect by light having a wavelength within the range of 350 nm to 400 nm inclusive, it is effective to use a lamp that emits light having that wavelength and eyeglasses with lenses through which that light is transmitted, in combination.

Figure 9:
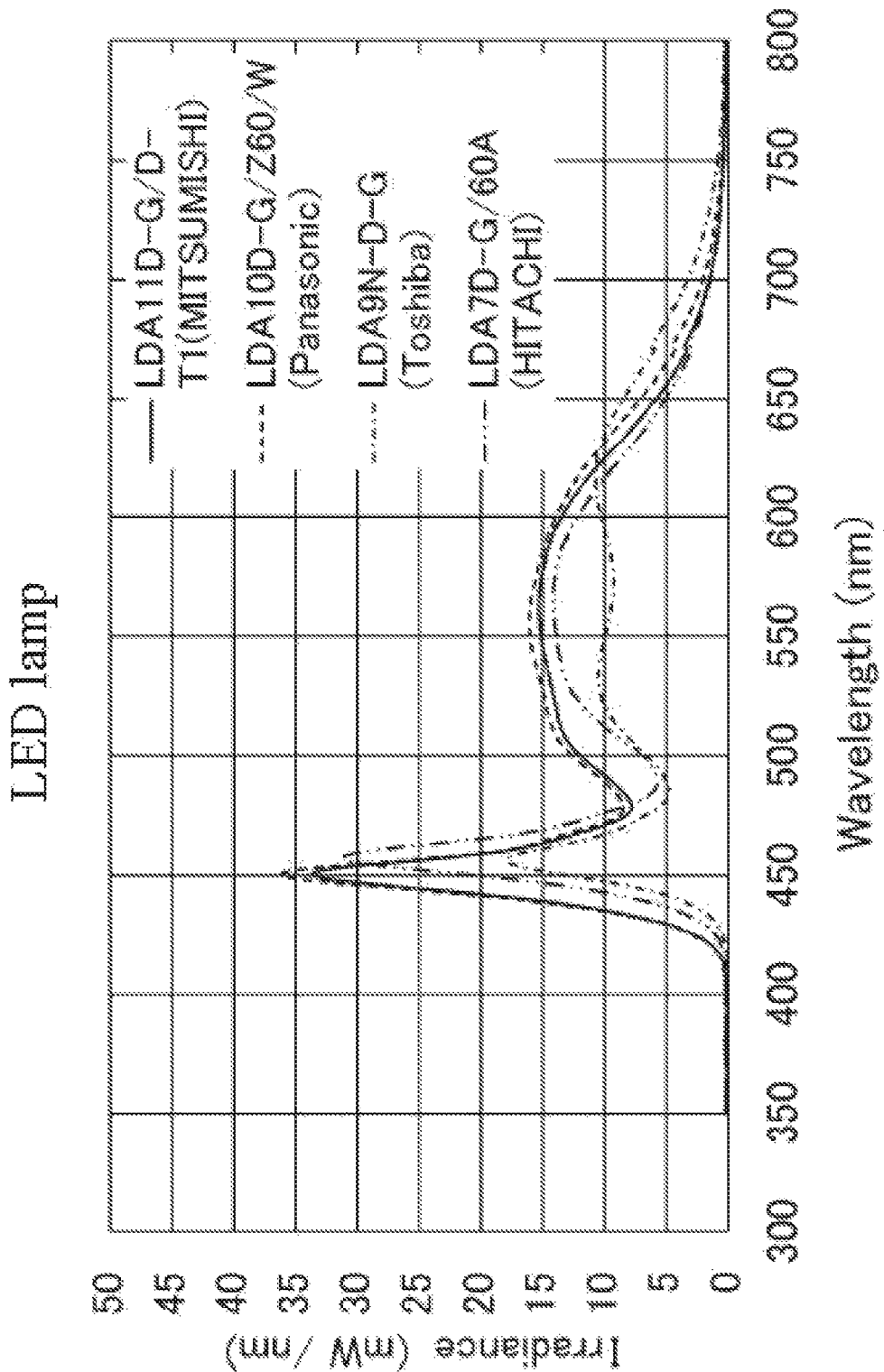
FIG. 9 is an example of an optical spectrum of an LED lamp that does not emit light having a wavelength of 400 nm or less and does not have a myopia suppression effect in Example 4.
Figure 10:
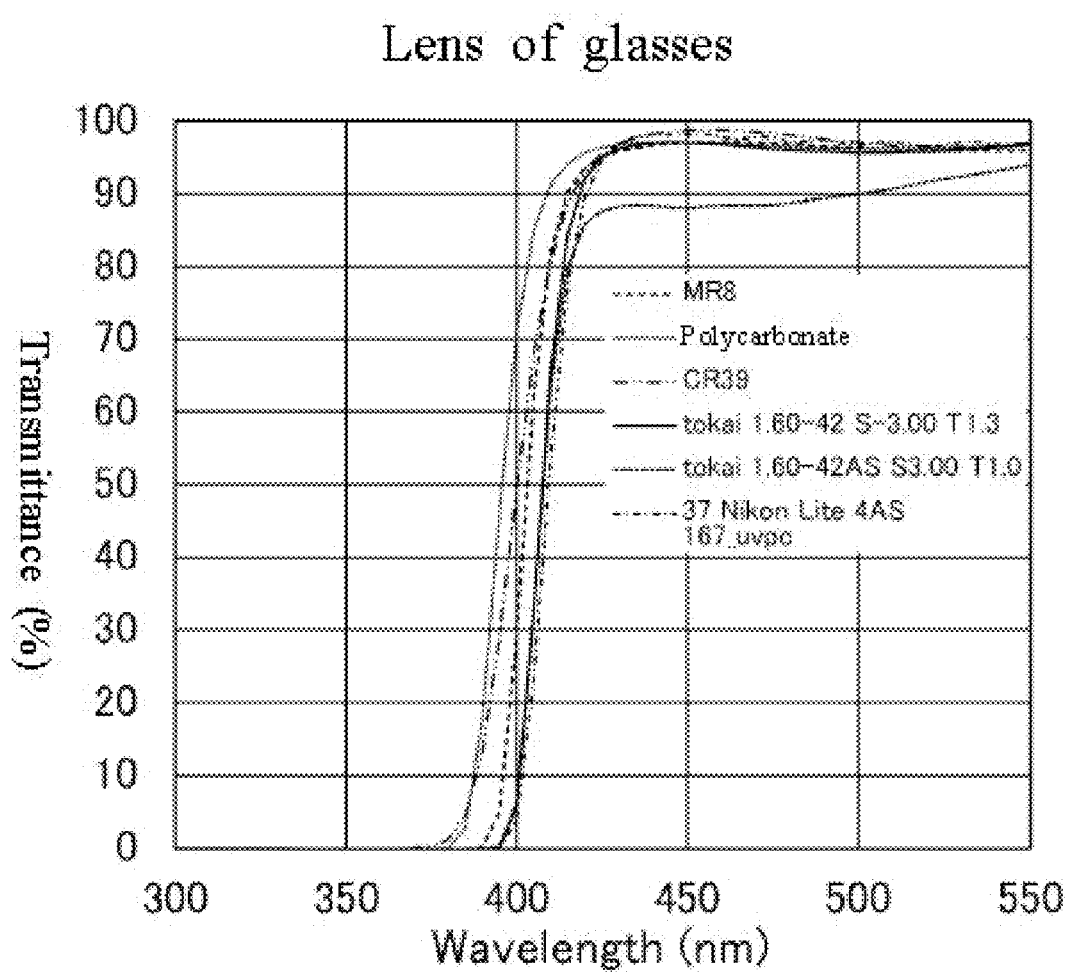
FIG. 10 is an example of an optical spectrum of an eyeglass lens that does not transmit light having a wavelength of 400 nm or less and does not have a myopia suppression effect in Example 4.

The lamps and glasses already on the market do not exhibit the effect of the present invention. For example, FIG. 9 shows the optical spectrum of an LED lamp that does not or substantially does not emit light having a wavelength of 400 nm or less or does not emit light having a peak in the wavelength region of 400 nm or less, and does not have a myopia suppression effect. FIG. 10 shows a transmittance light spectrum of an eyeglass lens that does not or substantially does not transmit light having a wavelength of 400 nm or less, and does not have a myopia suppression effect. It should be noted that "substantially does not emit" and "substantially does not transmit" mean that the emission or transmission is significantly small compared to light of other regions.

Figure 12:
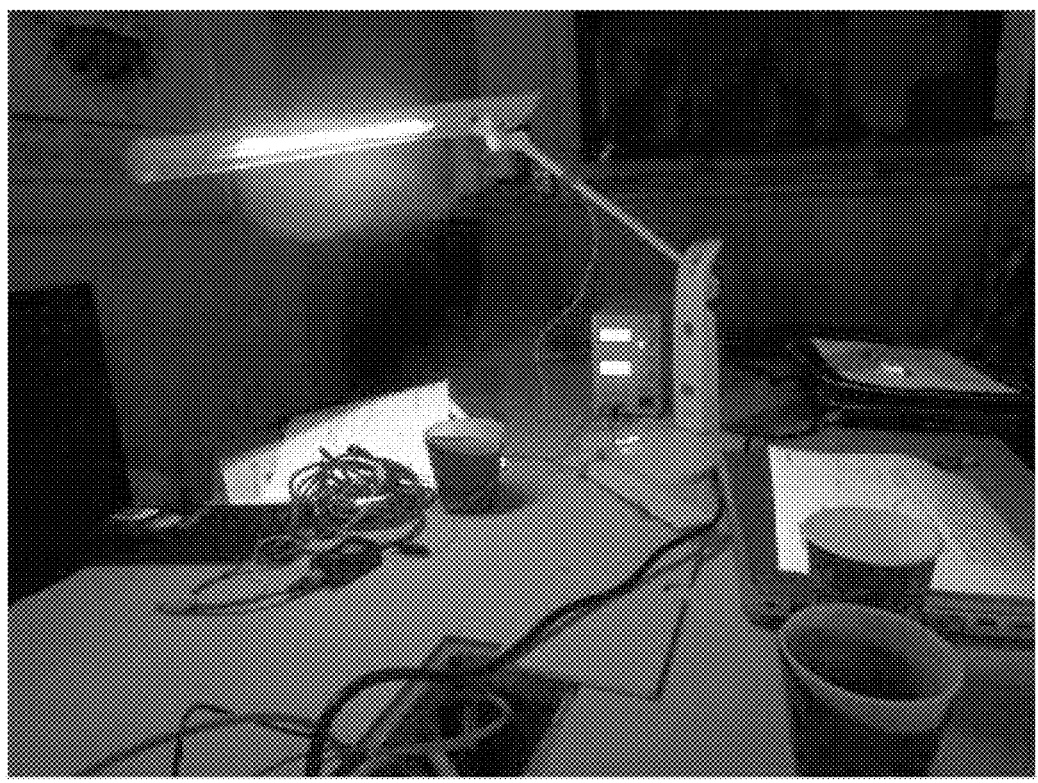
FIG. 12 is the lamp having the optical spectrum shown in FIG. 11, in Example 4.

On the other hand, FIG. 11 and FIG. 12 show an optical spectrum and an image of a lamp, respectively, as an example of the myopia prevention device of the present invention. The lamp shown in FIG. 12 uses a special LED that emits light having a wavelength effective for myopia prevention. Further, the lamp in FIG. 12 is capable of increasing (a) and decreasing (b) and thus changing the intensity of the 380 nm serving as the peak wavelength, as shown in FIG. 11. Such a lamp with a variable peak intensity makes it possible to control irradiation intensity as desired, and is therefore preferred from the viewpoint that the lamp can effectively prevent myopia.

The lamp shown in FIG. 4 and the lamp shown in FIG. 11 are both recognized as effective myopia prevention devices, and thus the myopia prevention device of the present invention preferably includes the light emission part that emits light having a wavelength of 350 nm to 400 nm inclusive and a peak wavelength within the range of 365 nm (FIGS. 4) to 380 nm (FIG. 11). At this time, light having a wavelength less than 350 nm and light having a wavelength of 315 nm or less in particular are preferably not or substantially not emitted. It should be noted that the light emitted from the lamps shown in FIG. 4 and FIG. 11 is not light having a peak wavelength less than 350 nm or light having a peak wavelength greater than 400 nm. Thus, "the light emission part that emits light having a wavelength of 350 nm to 400 nm inclusive and a peak wavelength within the range of 365 nm (FIG. 4) to 380 nm (FIG. 11)" does not emit light having a peak at a wavelength less than 350 nm or at a wavelength greater than 400 nm.

Figure 13:
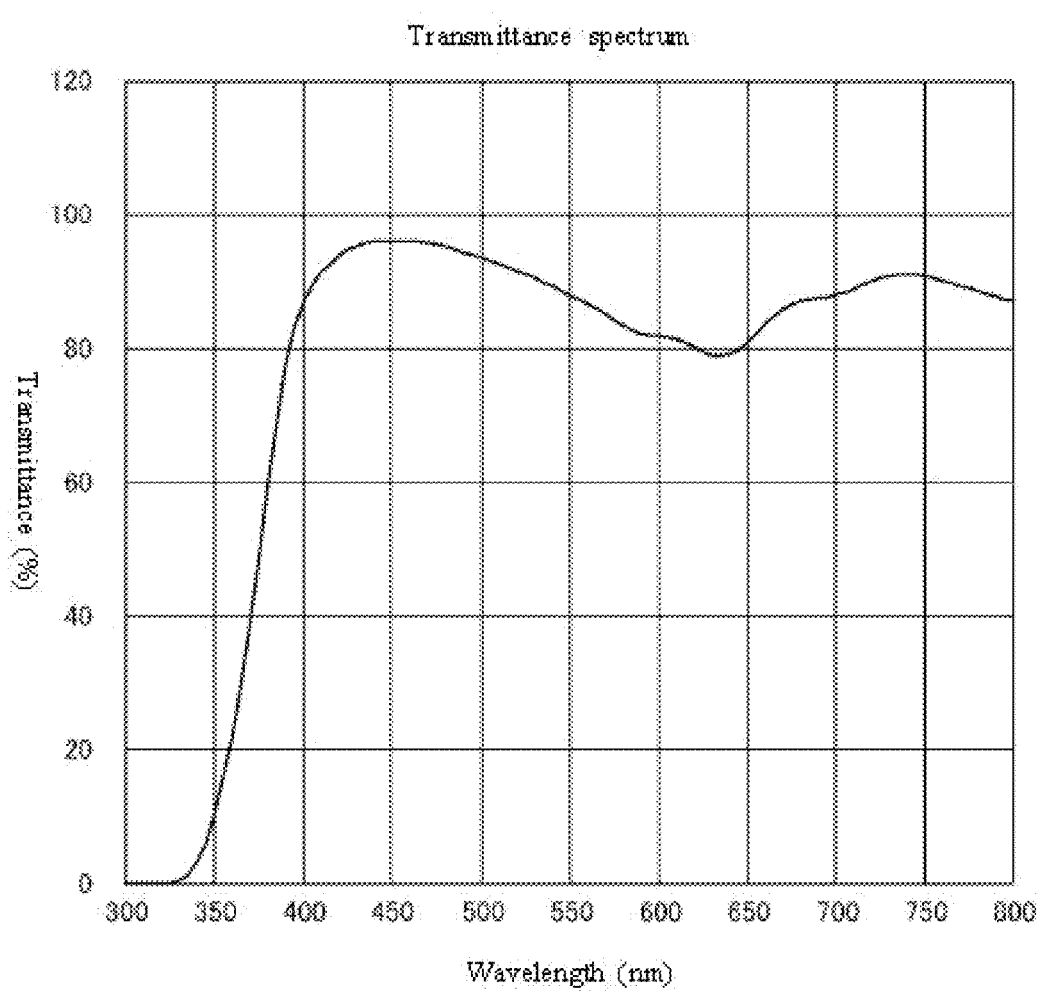
FIG. 13 is a transmittance spectrum of an eyeglass lens that transmits light having a wavelength within the range of 350 nm to 400 nm inclusive in Example 4.

FIG. 13 shows a transmittance spectrum of an eyeglass lens that transmits light having a wavelength effective for myopia prevention. Combined use of the glasses in FIG. 13 and the lamp shown in FIG. 11 makes it possible to effectively exhibit the myopia suppression effect.

Example 5

Figure 14:
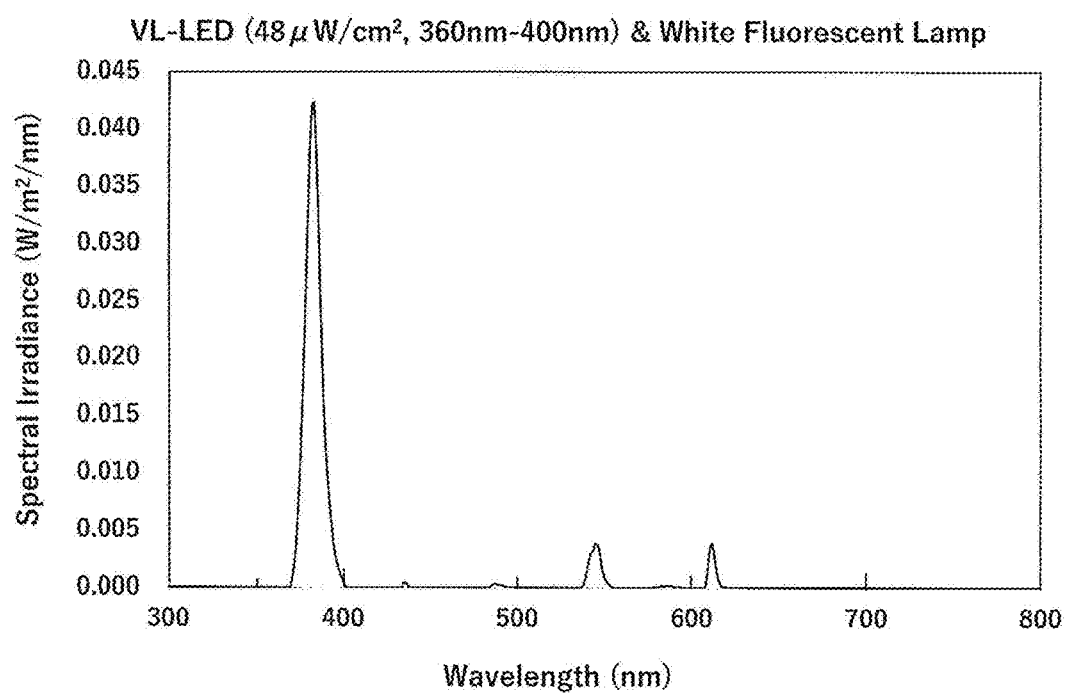
FIG. 14 is an optical spectrum of light irradiated at an irradiance of 0.048 mW/cm$^2$ in Example 5.
Figure 15:
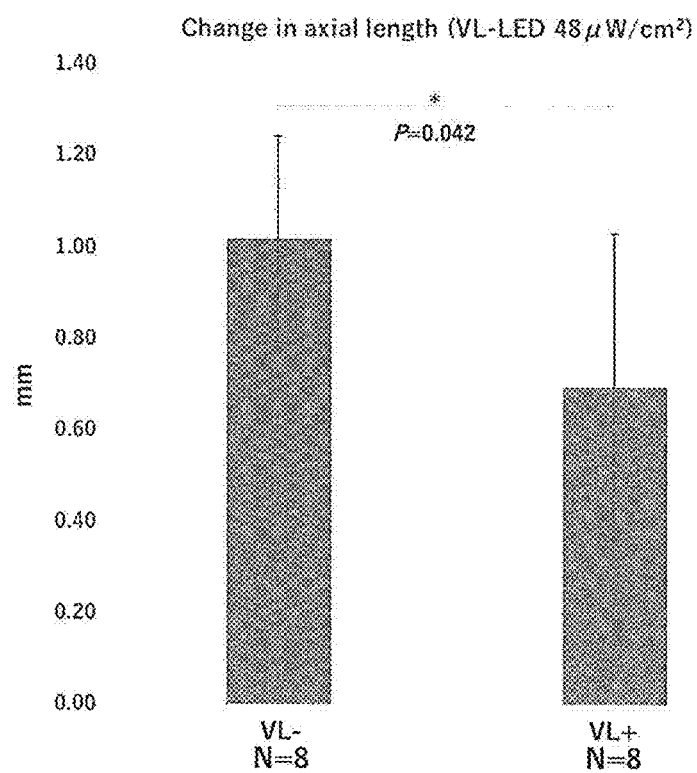
FIG. 15 shows the results of measuring a change in the axial length of the eye when irradiated with the light shown in FIG. 14, in Example 5.
Figure 16:
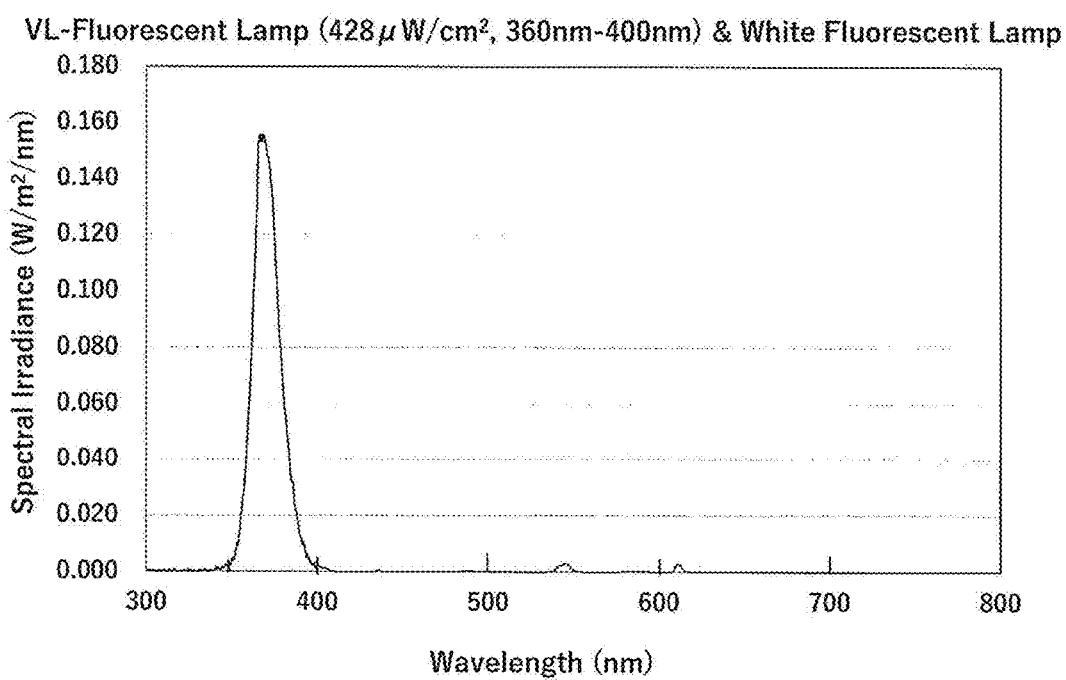
FIG. 16 is an optical spectrum of light irradiated at an irradiance of 0.428 mW/cm$^2$ in Example 5.
Figure 17:
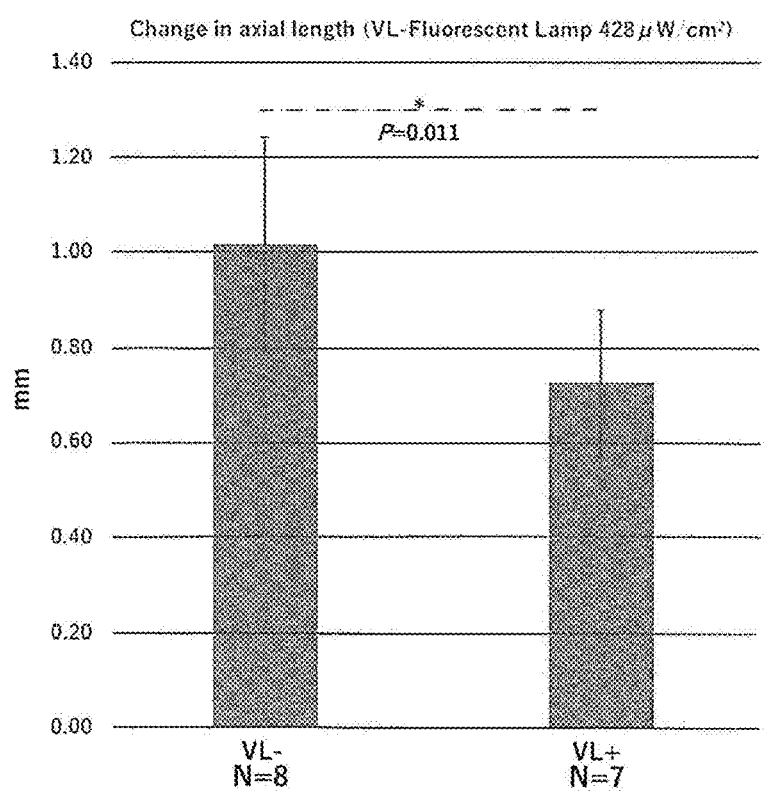
FIG. 17 shows the results of measuring a change in the axial length of the eye when irradiated with the light shown in FIG. 16, in Example 5.

Similar to Example 2, a test was conducted by changing the irradiance of light having a wavelength of 350 to 400 nm (peak wavelength: 365 nm) to 0.048 mW/cm$^2$ and 0.428 mW/cm$^2$. Similar to Example 2, the test was performed by inserting approximately eight chicks into individual cages having the dimensions of a 450-mm length, an 800-mm width, and a 250-mm height, and raising the chicks for one week spending 12 hours in the light and 12 hours in the dark each day. The degree of myopia development of the shielded eye was then examined. FIG. 14 shows an optical spectrum of the light irradiated at an irradiance of 0.048 mW/cm$^2$, and FIG. 15 shows the results of measuring the axial length of the eyes when the light shown in FIG. 14 was irradiated. Further, FIG. 16 shows an optical spectrum of the light irradiated at an irradiance of 0.428 mW/cm$^2$, and FIG. 17 shows the results of measuring the axial length of the eyes when the light shown in FIG. 16 was irradiated. Similar to Example 2, the axial length of the eye was measured using US-4000 (Nidek) in mode B.

CONCLUSION

When the eye is thus exposed to light having a wavelength within the range of 350 nm to 400 nm inclusive, it is possible to suppress the occurrence and progression of myopia in the eye.

INDUSTRIAL APPLICABILITY

According to the present invention, it becomes possible to provide a myopia prevention device.

What is claimed is:

1. A myopia prevention device, comprising:
a light transmission part selected from the group consisting of an eyesight correcting tool, an eye protection tool, a face protection tool, a sunshade, a display device, a window, a wall, a light source covering, and a coating material; the light transmission part of the device transmitting light having a wavelength within a range of 350 nm to 400 nm inclusive and thus suppressing the occurrence and progression of myopia,
wherein an irradiance at which the light having a wavelength within the range of 350 nm to 400 nm inclusive and transmitted by the light transmission part reaches an eye is 1.0 mW/cm$^2$ or less.

2. The myopia prevention device according to claim 1, wherein
the light transmission part does not transmit light having a wavelength of 315 nm or less.

3. The myopia prevention device according to claim 2, wherein
a transmission rate of the light having a wavelength of 315 nm or less is 1% or less.

4. The myopia prevention device according to claim 1, wherein
the light transmission part does not transmit light having a wavelength less than 350 nm.

5. The myopia prevention device according to claim 1, wherein
the light transmission part further transmits light having a wavelength greater than 400 nm.

6. A myopia prevention device, comprising:
a light emission part selected from the group consisting of lighting equipment, a display device, and a light irradiation device; the light emission part of the device emitting light having a wavelength within a range of 350 nm to 400 nm inclusive and thus suppressing the occurrence and progression of myopia,
wherein an irradiance at which the light having a wavelength within the range of 350 nm to 400 nm inclusive and emitted by the light emission part reaches an eye is 1.0 mW/cm$^2$ or less.

7. The myopia prevention device according to claim 6, wherein
the light emission part further emits light having a wavelength greater than 400 nm.

8. The myopia prevention device according to claim 6, further comprising a light-emitting device comprising an excitation light emission part that emits excitation light having a wavelength within a range of 350 nm to 400 nm inclusive, and fluorescent substances of red, green, and blue provided so as to cover the excitation light emission part.

9. The myopia prevention device according to claim 6, further comprising a light-emitting device comprising a light emission part that emits light having a wavelength within a range of 350 nm to 400 nm inclusive, and light emission parts of red, green, and blue.

10. A set, comprising:
a first myopia prevention device comprising a light transmission part selected from the group consisting of an eyesight correcting tool, an eye protection tool, a face protection tool, a sunshade, a display device, a window, a wall, a light source covering, and a coating material, the light transmission part of the first myopia prevention device transmitting light having a wavelength within a range of 350 nm to 400 nm inclusive and thus suppressing the occurrence and progression of myopia; and
a second myopia prevention device comprising a light emission part selected from the group consisting of lighting equipment, a display device, and a light irradiation device, the light emission part of the second myopia prevention device emitting light having a wavelength within a range of 350 nm to 400 nm inclusive and thus suppressing the occurrence and progression of myopia,
wherein in each of the first and second myopia prevention devices, an irradiance at which the light having a wavelength within the range of 350 nm to 400 nm inclusive and transmitted or emitted by the light transmission part or the light emission part reaches an eye is 1.0 mW/cm$^2$ or less.

* * * * *